United States Patent
Powers et al.

(10) Patent No.: US 7,492,144 B2
(45) Date of Patent: *Feb. 17, 2009

(54) PREVENTING FALSE LOCKS IN A SYSTEM THAT COMMUNICATES WITH AN IMPLANTED WIRELESS SENSOR

(75) Inventors: Richard Powers, Atlanta, GA (US);
Michael G. Ellis, Alpharetta, GA (US);
Jason Kroh, Villa Rica, GA (US);
Donald J. Miller, Roswell, GA (US)

(73) Assignee: CardioMEMS, Inc., Atlanta, GA (US)

( * ) Notice: Subject to any disclaimer, the term of this patent is extended or adjusted under 35 U.S.C. 154(b) by 176 days.

This patent is subject to a terminal disclaimer.

(21) Appl. No.: 11/470,465

(22) Filed: Sep. 6, 2006

(65) Prior Publication Data
US 2007/0100215 A1 May 3, 2007

Related U.S. Application Data

(60) Provisional application No. 60/714,472, filed on Sep. 6, 2005, provisional application No. 60/715,273, filed on Sep. 8, 2005.

(51) Int. Cl.
*G01R 23/12* (2006.01)
(52) U.S. Cl. .................. 324/76.52; 324/76.53
(58) Field of Classification Search ............. 324/76.52, 324/76.39, 76.11, 76.53, 76.51, 76.77, 601; 327/3, 20, 33, 47
See application file for complete search history.

(56) References Cited

U.S. PATENT DOCUMENTS 3,882,424 A 5/1975 Debois et al.
3,913,028 A * 10/1975 Bosselaers ............... 331/1 A (Continued)

FOREIGN PATENT DOCUMENTS

WO    WO 97/11641 A    4/1997

(Continued)

OTHER PUBLICATIONS

Allen, "Micromachined Endovascularly Implantable Wireless Aneurysm Pressure Sensors", International Conference on Solid State Sensors, Actuators and Microsystems, No. 13, 2005, pp. 275-278.

(Continued)

*Primary Examiner*—Diego Gutierrez
*Assistant Examiner*—Hoai-An D Nguyen
(74) *Attorney, Agent, or Firm*—Kilpatrick Stockton LLP

(57) ABSTRACT

The present invention determines the resonant frequency of a wireless sensor by adjusting the phase and frequency of an energizing signal until the frequency of the energizing signal matches the resonant frequency of the sensor. The system energizes the sensor with a low duty cycle, gated burst of RF energy having a predetermined frequency. The system receives the ring down response of the sensor and determines the resonant frequency of the sensor, which is used to calculate a physical parameter. The system uses a pair of phase locked loops to adjust the phase and the frequency of the energizing signal. The system identifies false locks by detecting an unwanted beat frequency in the coupled signal, as well as determining whether the coupled signal exhibits pulsatile characteristics that correspond to a periodic physiological characteristic, such as blood pressure.

15 Claims, 10 Drawing Sheets

U.S. PATENT DOCUMENTS

| | | | |
|---|---|---|---|
| 4,114,606 A | 9/1978 | Seylar | |
| 4,152,669 A | 5/1979 | Igarashi | |
| 4,531,526 A | 7/1985 | Genest | |
| 4,593,703 A | 6/1986 | Cosman et al. | |
| 4,720,687 A * | 1/1988 | Ostoich et al. | 331/1 A |
| 5,148,123 A * | 9/1992 | Ries | 331/4 |
| 5,594,389 A | 1/1997 | Kiyanagi et al. | |
| 5,625,341 A | 4/1997 | Giles et al. | |
| 5,896,113 A | 4/1999 | O'Neill | |
| 6,111,520 A | 8/2000 | Allen et al. | |
| 6,165,135 A | 12/2000 | Neff | |
| 6,237,398 B1 | 5/2001 | Porat et al. | |
| 6,259,328 B1 | 7/2001 | Wesolowski | |
| 6,278,379 B1 | 8/2001 | Allen et al. | |
| 6,331,792 B1 * | 12/2001 | Tonietto | 327/48 |
| 6,411,130 B1 * | 6/2002 | Gater | 327/12 |
| 6,577,893 B1 | 6/2003 | Besson et al. | |
| 6,743,183 B1 | 6/2004 | Thornton | |
| 6,855,115 B2 | 2/2005 | Fonseca et al. | |
| 7,076,215 B1 | 7/2006 | Moliere | |
| 7,233,182 B1 * | 6/2007 | Savoj | 327/141 |
| 7,245,117 B1 | 7/2007 | Joy et al. | |
| 2003/0136417 A1 | 7/2003 | Fonseca et al. | |
| 2003/0139677 A1 | 7/2003 | Fonseca et al. | |
| 2003/0151400 A1 | 8/2003 | Petrovich et al. | |
| 2003/0185330 A1 | 10/2003 | Hessel et al. | |
| 2006/0196277 A1 | 9/2006 | Allen et al. | |
| 2007/0096715 A1 | 5/2007 | Joy et al. | |
| 2007/0210786 A1 | 9/2007 | Allen et al. | |
| 2007/0247138 A1 | 10/2007 | Miller et al. | |

FOREIGN PATENT DOCUMENTS

| | | |
|---|---|---|
| WO | WO 98/47727 A | 10/1998 |
| WO | WO 03/032009 | 4/2003 |
| WO | WO 2005/027998 | 3/2005 |
| WO | WO 2006/049796 | 5/2006 |

OTHER PUBLICATIONS

Dehennis, "A Double-Sided Single-Chip Wireless Pressure Sensor", *IEEEMEMSCONF* 2002, pp. 252-255.

Fonseca, "High Temperature Characterization of Ceramic Pressure Sensors", vol. 1, 2001, pp. 486-489.

Harpster, "A Passive Wireless Integrated Humidity Sensor", Micro Electro Mechanical Systems, 2001, vol. IEEEMEMSCONF, No. 14, pp. 553-557.

Seifert, et al., "Wirelessly Interrogable Acoustic Sensors", Frequency and Time Form, (Online) No. 4, 1999, pp. 1013-1018.

* cited by examiner

PREVENTING FALSE LOCKS IN A SYSTEM THAT COMMUNICATES WITH AN IMPLANTED WIRELESS SENSOR

RELATED APPLICATIONS

This application claims priority to U.S. Provisional Application No. 60/714,472 entitled "Communicating with an Implanted Wireless Sensor" filed Sep. 6, 2005 and U.S. Provisional Application No. 60/715,273 entitled "Low Frequency Tone Detect Algorithm for Detection of Physiological Signals Using a Wireless Pressure Sensing System" filed Sep. 8, 2005, both of which are incorporated herein by reference.

This application is related to U.S. application Ser. No. 11/276,571 entitled "Communicating with an Implanted Wireless Sensor" filed Mar. 6, 2006 (the "'571 Application") and U.S. application Ser. No. 11/105,294 entitled "Communicating with an Implanted Wireless Sensor" filed Apr. 13, 2005, both of which are incorporated herein by reference.

TECHNICAL FIELD

The present invention is directed in general to communicating with a wireless sensor, and in particular to preventing false locks in a system that communicates with a wireless sensor implanted within the body to measure a physical condition.

BACKGROUND

Wireless sensors can be implanted within the body and used to monitor physical conditions, such as pressure or temperature. For example, U.S. Pat. Nos. 6,111,520, 6,855,115 and U.S. Publication No. 2003/0136417, each of which is incorporated herein by reference, all describe wireless sensors that can be implanted within the body. These sensors can be used to monitor physical conditions within the heart or an abdominal aneurysm. An abdominal aortic aneurysm (AAA) is a dilatation and weakening of the abdominal aorta that can lead to aortic rupture and sudden death. In the case of a repaired abdominal aneurysm, a sensor can be used to monitor pressure within the aneurysm sac to determine whether the intervention is leaking. The standard treatment for AAAs employs the use of stent-grafts that are implanted via endovascular techniques. However, a significant problem that has emerged with these stent-grafts for AAAs is acute and late leaks of blood into the aneurysms sac. Currently, following stent-graft implantation, patients are subjected to periodic evaluation via abdominal CT (Computed Tomography) with IV contrast to identify the potential presence of stent-graft leaks. This is an expensive, risky procedure that lacks appropriate sensitivity to detect small leaks.

Typically, the sensors utilize an inductive-capacitive ("LC") resonant circuit with a variable capacitor. The capacitance of the circuit varies with the pressure of the environment in which the sensor is located and thus, the resonant frequency of the circuit varies as the pressure varies. Thus, the resonant frequency of the circuit can be used to calculate pressure.

Ideally, the resonant frequency is determined using a non-invasive procedure. Several examples of procedures for determining the resonant frequency of an implanted sensor are discussed in U.S. Pat. No. 6,111,520. Some of the procedures described in the patent require the transmission of a signal having multiple frequencies. A drawback of using a transmission signal having multiple frequencies is that the energy in the frequency bands outside the resonant frequency is wasted. This excess energy requires more power which results in an increase in cost, size, and thermal requirements, as well as an increase in electromagnetic interference with other signals. Thus, there is a need for an optimized method that is more energy efficient and requires less power.

There are unique requirements for communicating with an implanted sensor. For example, the system must operate in a low power environment and must be capable of handling a signal from the sensor with certain characteristics. For example, the signal from the sensor is relatively weak and must be detected quickly because the signal dissipates quickly. These requirements also impact the way that common problems are handled by the system. For example, the problem of false locking needs to be handled in a manner that accommodates the sensor signal characteristics. Thus, there is a need for a method for communicating with a wireless sensor that operates in a low power environment, that efficiently determines the resonant frequency of the sensor and that handles false locks.

The resonant frequency of the sensor is a measured parameter that is correlated with the physical parameter of interest. To be clinically useful there must be means to ensure that variations in measurement environment do not affect the accuracy of the sensor. Thus, there is a need for a system and method for communicating with a wireless sensor that considers variations in the measurement environment.

SUMMARY OF THE INVENTION

The primary goal of aneurysm treatment is to depressurize the sac and to prevent rupture. Endoleaks, whether occurring intraoperatively or postoperatively, can allow the aneurysmal sac to remain pressurized and therefore, increase the chance of aneurysm rupture. The current imaging modalities angiography and CT scan are not always sensitive enough to detect endoleaks or stent graft failure. Intrasac pressure measurements provide a direct assessment of sac exclusion from circulation and may therefore offer intraoperative and post operative surveillance advantages that indirect imaging studies do not.

In one application of the present invention, a AAA pressure sensor is placed into the aneurysm sac at the time of stent-graft insertion. The pressure readings are read out by the physician by holding an electronic instrument, which allows an immediate assessment of the success of the stent-graft at time of the procedure and outpatient follow-up visits, by reading the resonant frequency of the wireless sensor and correlating the frequency reading to pressure.

The present invention meets the needs described above by providing a system and method for communicating with a wireless sensor to determine the resonant frequency of the sensor. The system energizes the sensor with a low duty cycle, gated burst of RF energy having a predetermined frequency or set of frequencies and a predetermined amplitude. The energizing signal is coupled to the sensor via a magnetic loop. The sensor may be an inductive-capacitive ("LC") resonant circuit with a variable capacitor that is implanted within the body and used to measure physical parameters, such as pressure or temperature. The energizing signal induces a current in the sensor which is maximized when the energizing frequency is the same as the resonant frequency of the sensor. The system receives the ring down response of the sensor via magnetic coupling and determines the resonant frequency of the sensor, which is used to calculate the measured physical parameter.

A pair of phase locked loops ("PLLs") is used to adjust the phase and the frequency of the energizing signal until its frequency locks to the resonant frequency of the sensor. In one embodiment, one PLL samples during the calibration cycle and the other PLL samples during the measurement cycle. These cycles alternate every 10 microseconds synchronized with the pulse repetition period. The calibration cycle adjusts the phase of the energizing signal to a fixed reference phase to compensate for system delay or varying environmental conditions. The environmental conditions that can affect the accuracy of the sensor reading include, but are not limited to, proximity of reflecting or magnetically absorptive objects, variation of reflecting objects located within transmission distance, variation of temperature or humidity which can change parameters of internal components, and aging of internal components.

One of the PLLs is used to adjust the phase of the energizing signal and is referred to herein as the fast PLL. The other PLL is used to adjust the frequency of the energizing signal and is referred to herein as the slow PLL. During the time that the energizing signal is active, a portion of the signal enters the receiver and is referred to herein as a calibration signal. The calibration signal is processed and sampled to determine the phase difference between its phase and the phase of a local oscillator (referred to herein as the local oscillator 2). The cycle in which the calibration signal is sampled is referred to as the calibration cycle. The system adjusts the phase of the energizing signal to drive the phase difference to zero or another reference phase.

During the measurement cycle, the signal coupled from the sensor (referred to herein as the coupled signal or the sensor signal) is processed and sampled to determine the phase difference between the coupled signal and the energizing signal. The system then adjusts the frequency of the energizing signal to drive the phase difference to zero or other reference phase. Once the slow PLL is locked, the frequency of the energizing signal is deemed to match the resonant frequency of the sensor. The operation of the slow PLL is qualified based on signal strength so that the slow PLL does not lock unless the strength of the coupled signal meets a predetermined signal strength threshold.

The invention provides unique solutions to the problem of false locks. A false lock occurs if the system locks on a frequency that does not correspond to the resonant frequency of the sensor. In one aspect of the invention, the system handles false locks by detecting an unwanted beat frequency in the sensor signal. The coupled signal is processed and the phase of the signal is sampled multiple times. The multiple sampling points are averaged and the average indicates whether a beat frequency is present. If the average is non-zero, then there is no beat frequency and the lock is a true lock, i.e. the frequency of the energizing signal can be used to determine the resonant frequency of the sensor. If the average is zero or greater, then a beat frequency is detected and the lock is a false lock.

In another aspect of the invention, the system identifies a false lock caused by room reflection or resonance by determining whether the coupled signal is pulsatile in nature. Since the sensor is implanted in the body, the sensor signal is typically pulsatile in nature due to a periodic physiological characteristic, such as the patient's blood pressure. The coupled signal is processed and the energy in different frequency bands is compared to determine whether the signal is pulsatile and whether the pulsatile nature of the signal corresponds to the periodic physiological characteristic, such as the blood pressure waveform. If the coupled signal is pulsatile, then the lock is likely a true lock. If the coupled signal is not pulsatile, then the lock is likely a false lock.

The indication that the lock is false lock in either aspect of the invention that identifies false locks can be used to prevent the system from locking, to allow the system to lock, but to provide an indication to the physician using the system, or to allow the system to lock, but prevent the output from the system from being used.

These and other aspects, features and advantages of the present invention may be more clearly understood and appreciated from a review of the following detailed description of the disclosed embodiments and by reference to the appended drawings and claims.

DETAILED DESCRIPTION

The present invention is directed towards a system and method for communicating with a wireless sensor. Briefly described, the present invention determines the resonant frequency of the sensor by adjusting the phase and frequency of an energizing signal until the frequency of this signal locks to the resonant frequency of the sensor. The system energizes the sensor with a low duty cycle, gated burst of RF energy of a predetermined frequency or set of frequencies and predetermined amplitude. This signal induces a current in the sensor that can be used to track the resonant frequency of the sensor. The system receives the ring down response of the sensor and determines the resonant frequency of the sensor, which is used to calculate the measured physical parameter. The system uses a pair of phase locked loops ("PLL"s) to adjust the phase and the frequency of the energizing signal to track the resonant frequency of the sensor. The system identifies false locks by detecting an unwanted beat frequency and detecting whether the sensor signal includes pulsatile characteristics corresponding to blood pressure.

Exemplary System

Figure 1:
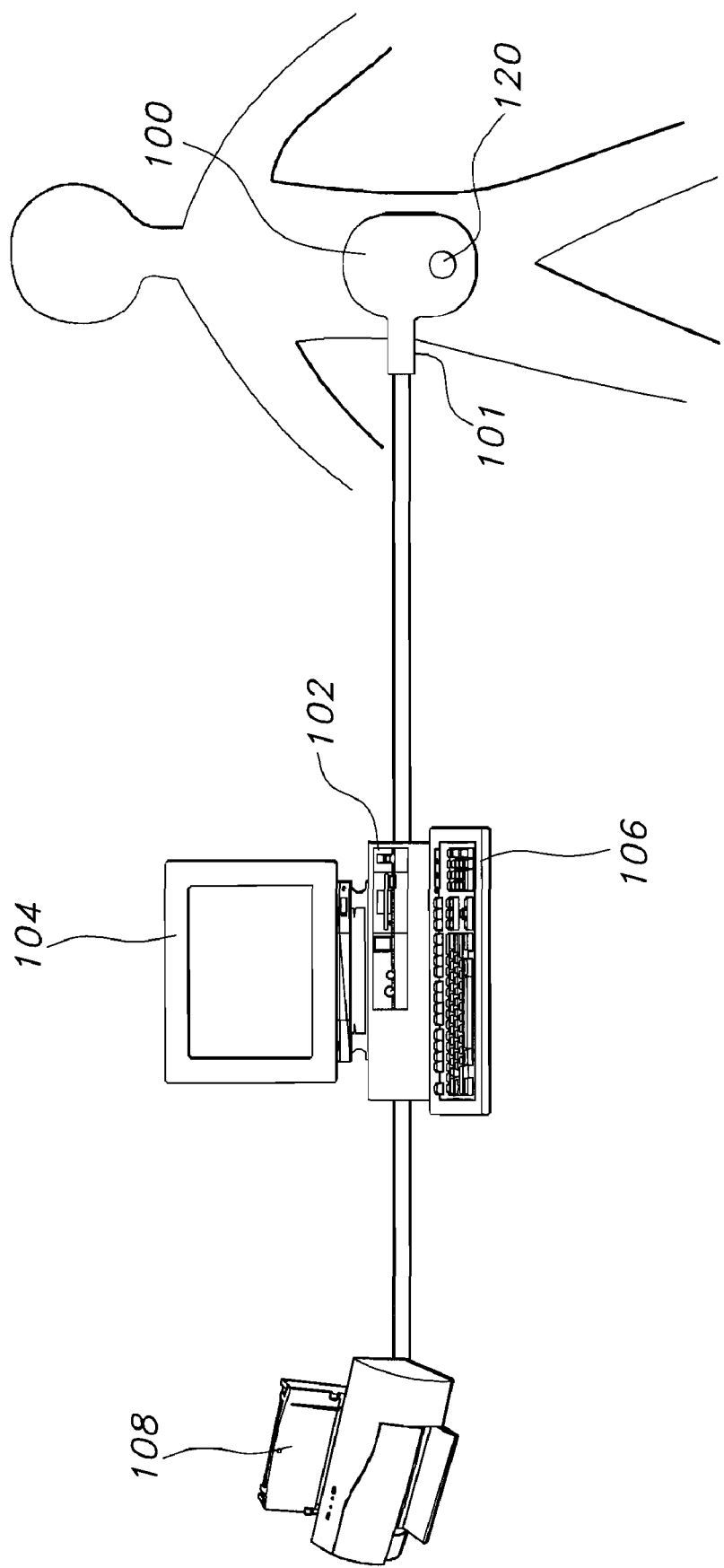
FIG. 1 is a block diagram of an exemplary system for communicating with a wireless sensor in accordance with an embodiment of the invention.

FIG. 1 illustrates an exemplary system for communicating with a wireless sensor implanted within a body. The system includes a coupling loop 100, a base unit 102, a display device 104 and an input device 106, such as a keyboard. The loop charges the sensor and then couples signals from the sensor into the receiver. Exemplary coupling loops are described in more detail in the '571 Application and U.S. application Ser. No. 11/479,527 entitled "Coupling Loop and Method for Positioning Coupling Loop" filed Jun. 30, 2006, which is incorporated herein by reference. The base unit includes an RF amplifier, a receiver, and signal processing circuitry. Additional details of the circuitry are described below in connection with FIG. 3.

The display 104 and the input device 106 are used in connection with the user interface for the system. In the embodiment illustrated in FIG. 1 the display device and the input device are connected to the base unit. In this embodiment, the base unit also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface. In one embodiment, LABVIEW software is used to provide the user interface, as well as to provide graphics, store and organize data and perform calculations for calibration and normalization. The user interface records and displays patient data and guides the user through surgical and follow-up procedures.

An optional printer 108 is connected to the base unit and can be used to print out patient data or other types of information. As will be apparent to those skilled in the art other configurations of the system, as well as additional or fewer components can be utilized with the invention.

Patient and system information can be stored within a removable data storage unit, such as a portable USB storage device, floppy disk, smart card, or any other similar device. The patient information can be transferred to the physician's personal computer for analysis, review, or storage. An optional network connection can be provided to automate storage or data transfer. Once the data is retrieved from the system, a custom or third party source can be employed to assist the physician with data analysis or storage.

FIG. 1 illustrates the system communicating with a sensor 120 implanted in a patient. The system is used in two environments: 1) the operating room during implant and 2) the doctor's office during follow-up examinations. During implant the system is used to record at least two measurements. The first measurement is taken during introduction of the sensor for calibration and the second measurement is taken after placement for functional verification of the stent graft. The measurements can be taken by placing the coupling loop either on or adjacent to the patient's back or the patient's stomach for a sensor that measures properties associated with an abdominal aneurysm. For other types of measurements, the coupling loop may be placed in other locations. For example, to measure properties associated with the heart, the coupling loop can be placed on the patient's back or the patient's chest.

The system communicates with the implanted sensor to determine the resonant frequency of the sensor. As described in more detail in the patent documents referenced in the Background section, a sensor typically includes an inductive-capacitive ("LC") resonant circuit having a variable capacitor. The distance between the plates of the variable capacitor varies as the surrounding pressure varies. Thus, the resonant frequency of the circuit can be used to determine the pressure.

Figure 2A:
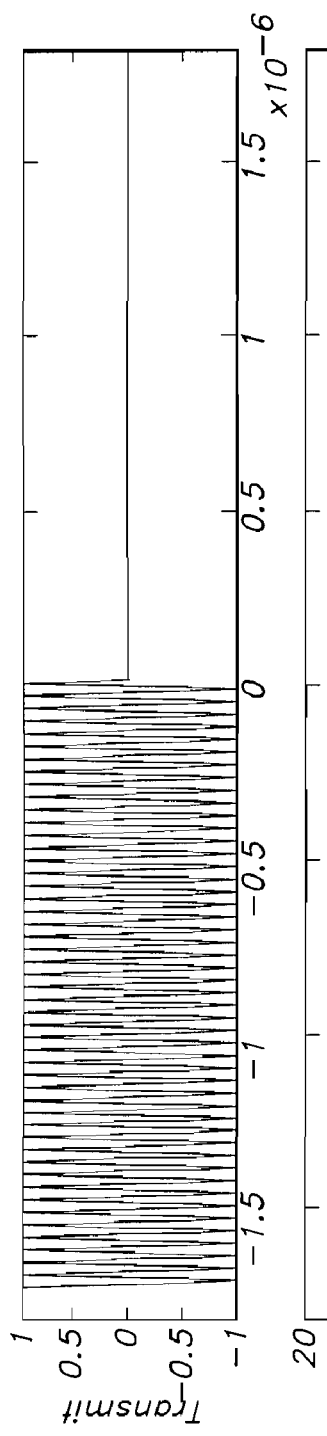
FIG. 2(a) is a graph illustrating an exemplary energizing signal in accordance with an embodiment of the invention.
Figure 2B:
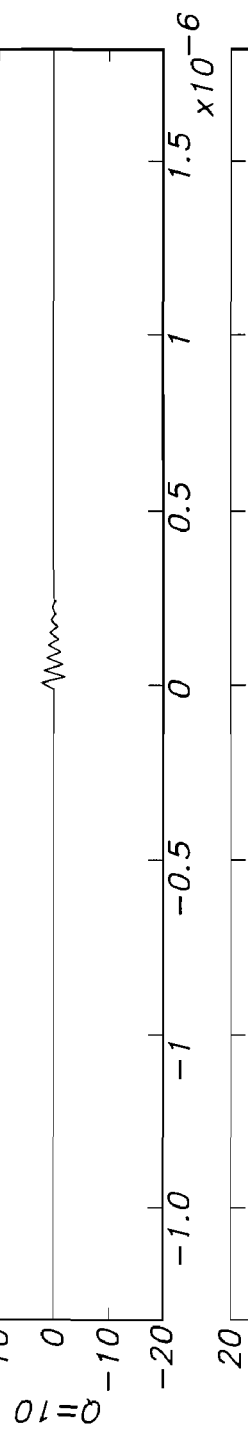
FIGS. 2(b), 2(c) and 2(d) are graphs illustrating exemplary coupled signals in accordance with an embodiment of the invention.
Figure 2C:
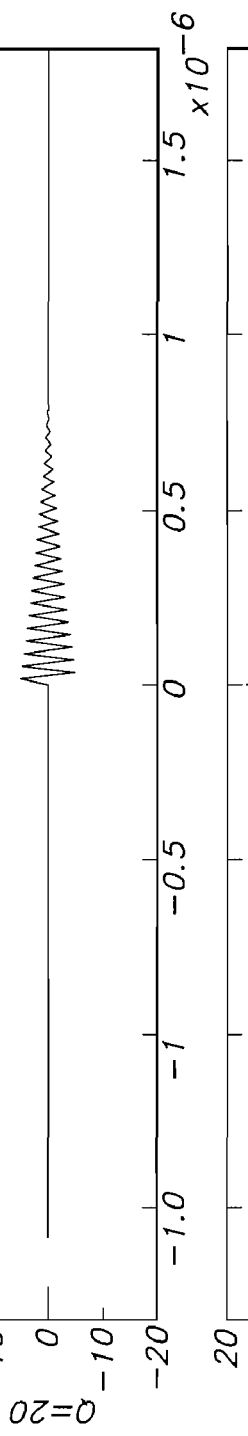
Figure 2D:
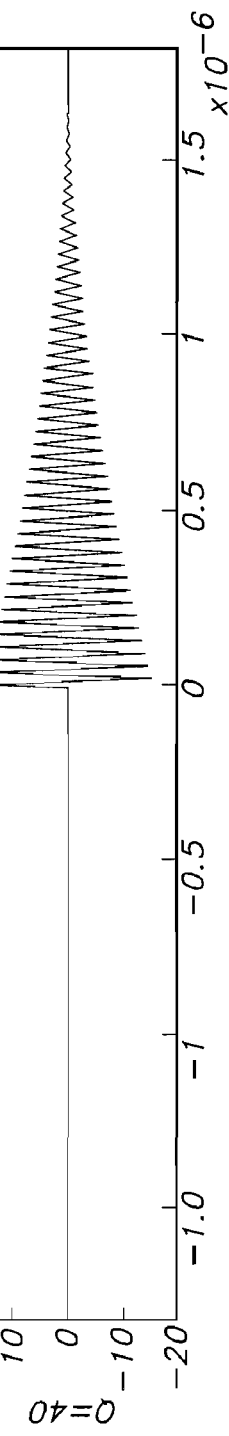
Figure 4:
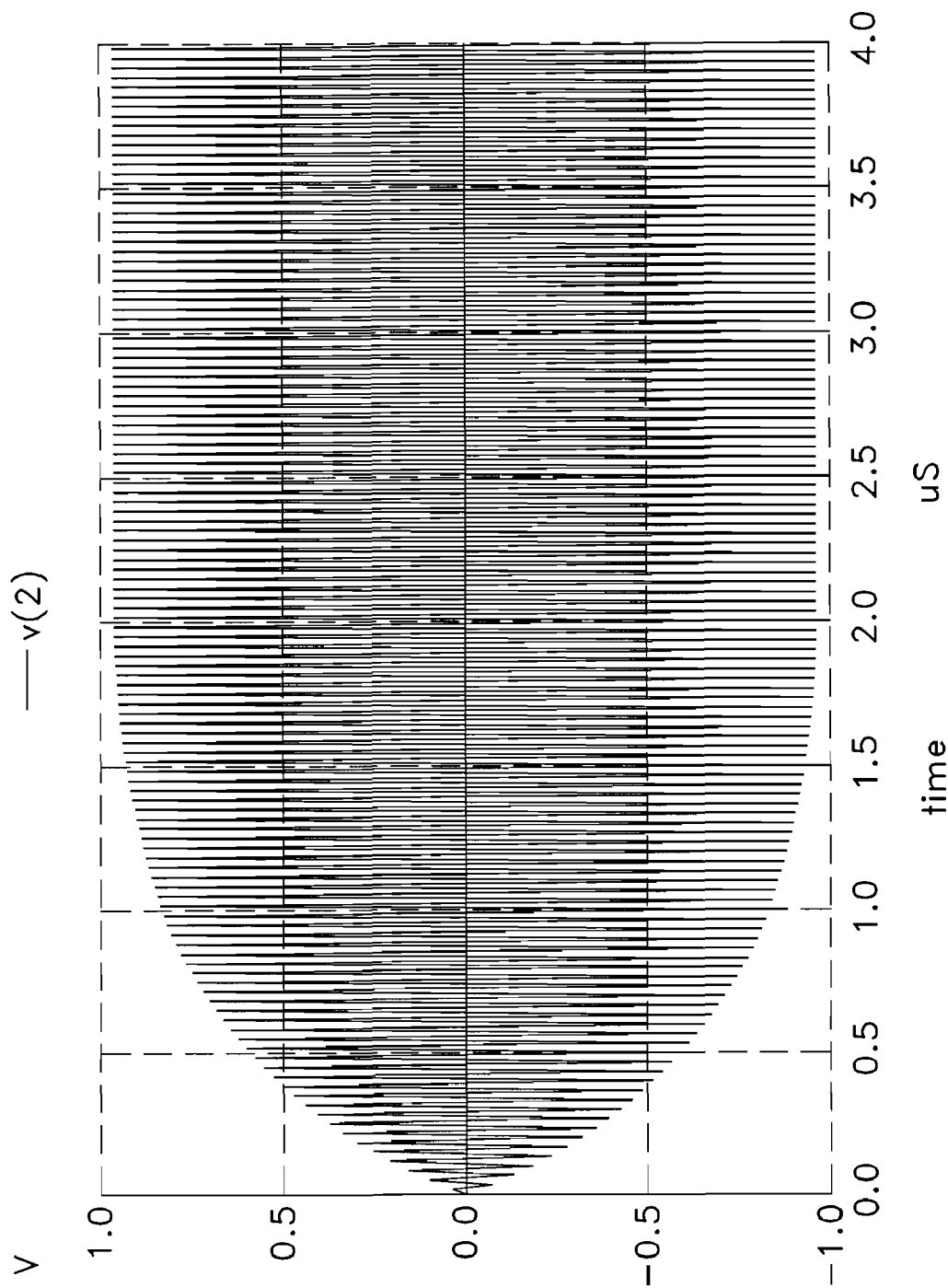
FIG. 4 is a graph illustrating an exemplary charging response of an LC circuit in accordance with an embodiment of the invention.

The system energizes the sensor with an RF burst. The energizing signal is a low duty cycle, gated burst of RF energy of a predetermined frequency or set of frequencies and a predetermined amplitude. Typically, the duty cycle of the energizing signal ranges from 0.1% to 50%. In one embodiment, the system energizes the sensor with a 30-37.5 MHz fundamental signal at a pulse repetition rate of 100 kHz with a duty cycle of 20%. The energizing signal is coupled to the sensor via a magnetic loop. This signal induces a current in the sensor which has maximum amplitude at the resonant frequency of the sensor. During this time, the sensor charges exponentially to a steady-state amplitude that is proportional to the coupling efficiency, distance between the sensor and loop, and the RF power. FIG. 4 shows the charging response of a typical LC circuit to a burst of RF energy at its resonant frequency. The speed at which the sensor charges is directly related to the Q (quality factor) of the sensor. Therefore, the "on time" of the pulse repetition duty cycle is optimized for the Q of the sensor. The system receives the ring down response of the sensor via magnetic coupling and determines the resonant frequency of the sensor. FIG. 2(a) illustrates a typical energizing signal and FIGS. 2(b), 2(c) and 2(d) illustrate typical coupled signals for various values of Q (quality factor) for the sensor. When the main unit is coupling energy at or near the resonant frequency of the sensor, the amplitude of the sensor return is maximized, and the phase of the sensor return will be close to zero degrees with respect to the energizing phase. The sensor return signal is processed via phase-locked-loops to steer the frequency and phase of the next energizing pulse.

Operation of the Base Unit

Figure 3:
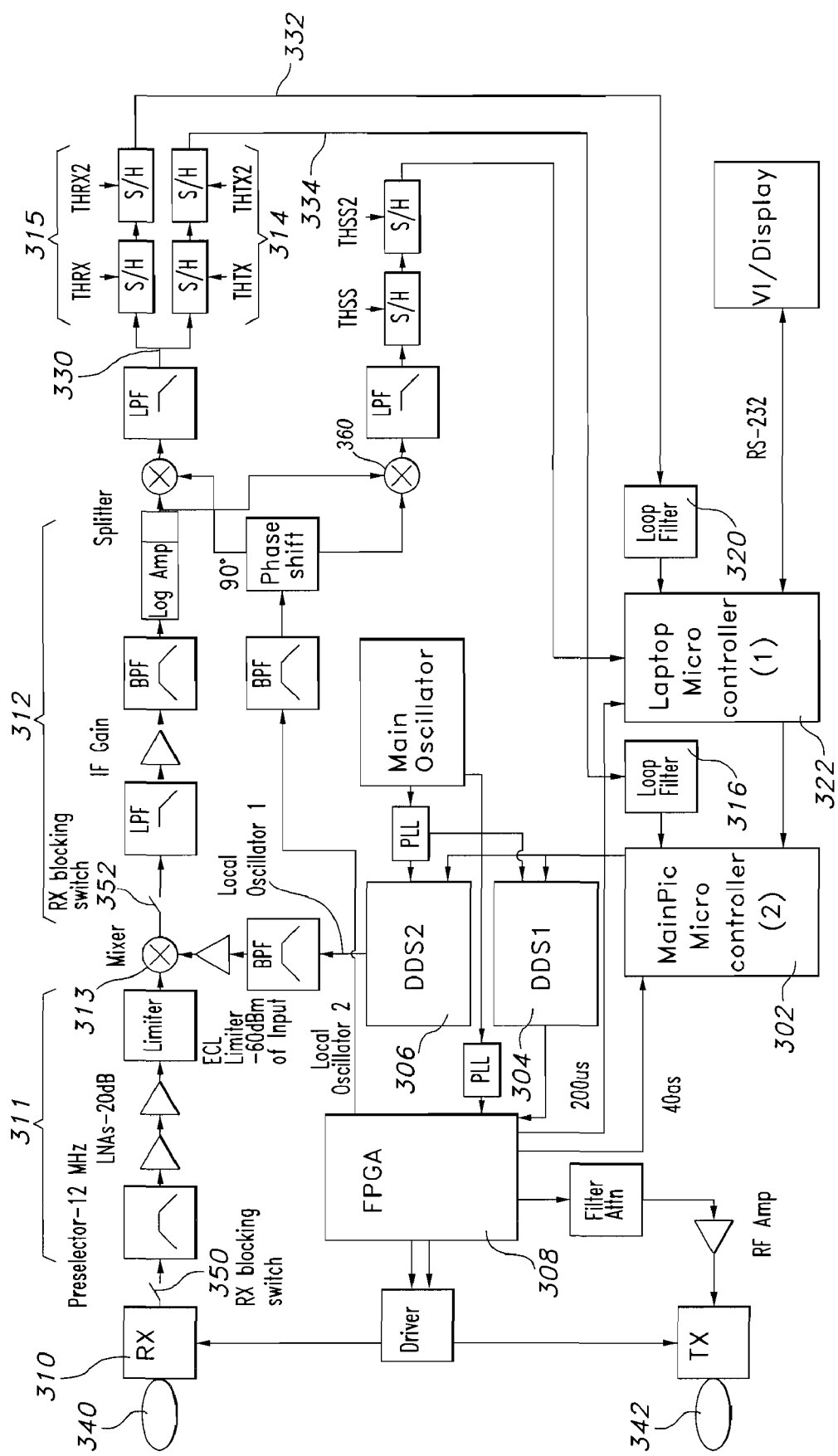
FIG. 3 is a block diagram of an exemplary base unit in accordance with an embodiment of the invention.

FIG. 3 is a block diagram of the signal processing components within an exemplary base unit. The base unit determines the resonant frequency of the sensor by adjusting the energizing signal so that the frequency of the energizing signal matches the resonant frequency of the sensor. In the embodiment illustrated by FIG. 3, two separate processors 302, 322 and two separate coupling loops 340, 342 are shown. In one embodiment, processor 302 is associated with the base unit and processor 322 is associated with a computer connected to the base unit. In other embodiments, a single processor is used that provides the same functions as the two separate processors. In other embodiments a single loop is used for both energizing and for coupling the sensor energy back to the receiver. As will be apparent to those skilled in the art, other configurations of the base unit are possible that use different components.

The embodiment illustrated by FIG. 3 includes a pair of phase lock loops ("PLL"). One of the PLLs is used to adjust the phase of the energizing signal and is referred to herein as the fast PLL. The other PLL is used to adjust the frequency of the energizing signal and is referred to herein as the slow PLL. The base unit provides two cycles: the calibration cycle and the measurement cycle. In one embodiment, the first cycle is a 10 microsecond energizing period for calibration of the system, which is referred to herein as the calibration cycle, and the second cycle is a 10 microsecond energizing/coupling period for energizing the sensor and coupling a return signal from the sensor, which is referred to herein as the measurement cycle. During the calibration cycle, the system generates a calibration signal for system and environmental phase calibration and during the measurement cycle the system both sends and listens for a return signal, i.e. the sensor ring down. Alternatively, as those skilled in the art will appreciate, the calibration cycle and the measurement cycle can be implemented in the same pulse repetition period.

The phase of the energizing signal is adjusted during the calibration cycle by the fast PLL and the frequency of the energizing signal is adjusted during the measurement cycle by the slow PLL. The following description of the operation of the PLLs is presented sequentially for simplicity. However, as those skilled in the art will appreciate, the PLLs actually operate simultaneously.

Initially the frequency of the energizing signal is set to a default value determined by the calibration parameters of the sensor. Each sensor is associated with a number of calibration parameters, such as frequency, offset, and slope. An operator of the system enters the sensor calibration parameters into the system via the user interface and the system determines an initial frequency for the energizing signal based on the particular sensor. Alternatively, the sensor calibration information could be stored on portable storage devices, bar codes, or incorporated within a signal returned from the sensor. The initial phase of the energizing signal is arbitrary.

The initial frequency and the initial phase are communicated from the processor 302 to the DDSs (direct digital synthesizers) 304, 306. The output of DDS1 304 is set to the initial frequency and initial phase and the output of DDS2 306 (also referred to as local oscillator 1) is set to the initial frequency plus the frequency of the local oscillator 2. The phase of DDS2 is a fixed constant. In one embodiment, the frequency of local oscillator 2 is 4.725 MHz. The output of DDS1 is gated by the field programmable gate array (FPGA) 308 to create a pulsed transmit signal having a pulse repetition frequency ("PRF"). The FPGA provides precise gating so that the base unit can sample the receive signal during specific intervals relative to the beginning or end of the calibration cycle.

During the calibration cycle, the calibration signal which enters the receiver 310 is processed through the receive section 311 and the IF section 312, and is sampled. In one embodiment, the calibration signal is the portion of the energizing signal that leaks into the receiver (referred to herein as the energizing leakage signal). The signal is sampled during the on time of the energizing signal by a sample and hold circuit 314 to determine the phase difference between the signal and local oscillator 2. FIG. 3 illustrates two cascaded sample and holds in circuit 314 to provide both fast sampling and a long hold time. Alternatively, a single sample and hold can be used in circuit 314. In the embodiment where the calibration signal is the portion of the energizing signal that leaks into the receiver, the signal is sampled approximately 100 ns after the beginning of the energizing signal pulse. Since the energizing signal is several orders of magnitude greater than the coupled signal, it is assumed that the phase information associated with the leaked signal is due to the energizing signal and the phase delay is due to the circuit elements in the coupling loop, circuit elements in the receiver, and environmental conditions, such as proximity of reflecting objects.

The phase difference is sent to a loop filter 316. The loop filter is set for the dynamic response of the fast PLL. In one embodiment, the PLL bandwidth is 1000 Hz and the damping ratio is 0.7. A DC offset is added to allow for positive and negative changes. The processor 302 reads its analog to digital converter (A/D) port to receive the phase difference information and adjusts the phase sent to direct digital synthesizer 1 (DDS1) to drive the phase difference to zero. This process is repeated alternatively until the phase difference is zero or another reference phase.

The phase adjustment made during the energizing period acts to zero the phase of the energizing signal with respect to local oscillator 2. Changes in the environment of the antenna or the receive chain impedance, as well as the phase delay within the circuitry prior to sampling affect the phase difference reading and are accommodated by the phase adjustment.

During the measurement cycle, the energizing signal may be blocked from the receiver during the on time of the energizing signal. During the off time of the energizing signal, the receiver is unblocked and the coupled signal from the sensor (referred to herein as the coupled signal or the sensor signal) is received. The coupled signal is amplified and filtered through the receive section 311. The signal is down converted and additional amplification and filtering takes place in the IF section 312. In one embodiment, the signal is down converted to 4.725 MHz. After being processed through the IF section, the signal is mixed with local oscillator 2 and sampled by sample and hold circuits 315 to determine the phase difference between the coupled signal and the energizing signal. FIG. 3 illustrates two cascaded sample and holds in circuit 315 to provide both fast sampling and a long hold time. Alternatively, a single sample and hold can be used in circuit 315. In one embodiment, the sampling occurs approximately 30 ns after the energizing signal is turned off.

In other embodiments, group delay or signal amplitude is used to determine the resonant frequency of the sensor. The phase curve of a second order system passes through zero at the resonant frequency. Since the group delay (i.e. the derivative of the phase curve) reaches a maximum at the resonant frequency, the group delay can be used to determine the resonant frequency. Alternatively, the amplitude of the sensor signal can be used to determine the resonant frequency. The sensor acts like a bandpass filter so that the sensor signal reaches a maximum at the resonant frequency.

The sampled signal is accumulated within a loop filter 320. The loop filter is set for the dynamic response of the slow PLL to aid in the acquisition of a lock by the slow PLL. The PLLs are implemented with op-amp low pass filters that feed A/D inputs on microcontrollers, 302 and 322, which in turn talk to the DDSs, 304 and 306, which provide the energizing signal and local oscillator 1. The microcontroller that controls the energizing DDS 304 also handles communication with the display. The response of the slow PLL depends upon whether the loop is locked or not. If the loop is unlocked, then the bandwidth is increased so that the loop will lock quickly. In one embodiment, the slow PLL has a damping ratio of 0.7 and a bandwidth of 120 Hz when locked (the Nyquist frequency of the blood pressure waveform), which is approximately ten times slower than the fast PLL.

A DC offset is also added to the signal to allow both a positive and a negative swing. The output of the loop filter is input to an A/D input of processor 322. The processor determines a new frequency and sends the new frequency to the DSSs. The processor offsets the current frequency value of the energizing signal by an amount that is proportional to the amount needed to drive the output of the slow PLL loop filter to a preset value. In one embodiment the preset value is 2.5V and zero in phase. The proportional amount is determined by the PLL's overall transfer function.

The frequency of the energizing signal is deemed to match the resonant frequency of the sensor when the slow PLL is locked. Once the resonant frequency is determined, the physical parameter, such as pressure, is calculated using the calibration parameters associated with the sensor, which results in a difference frequency that is proportional to the measured pressure.

The operation of the slow PLL is qualified based on signal strength. The base unit includes signal strength detection circuitry. If the received signal does not meet a predetermined signal strength threshold, then the slow PLL is not allowed to lock and the bandwidth and search window for the PLL are expanded. Once the received signal meets the predetermined signal strength threshold, then the bandwidth and search window of the slow PLL is narrowed and the PLL can lock. In the preferred embodiment, phase detection and signal strength determination are provided via the "I" (in phase) and "Q" (quadrature) channels of a quadrature mixer circuit. The "I" channel is lowpass filtered and sampled to provide signal strength information to the processing circuitry. The "Q" channel is lowpass filtered and sampled (THSS, THSS2) to provide phase error information to the slow PLL.

The base unit includes two switches, RX blocking switches 350 and 352, that aid in the detection of the sensor signal. One of the RX blocking switches precedes the preselector in the receive section 311 and the other RX blocking switch follows the mixer in the IF section 312. The FPGA controls the timing of the RX blocking switches (control signals not shown). The RX blocking switches are closed during the on time of the energizing signal during the calibration cycle and generally closed during the off time of the energizing signal during the measurement cycle. During the measurement cycle the timing of the RX blocking switches is similar to the timing of the switch that controls the energizing signal into the receiver during the measurement cycle, but the RX blocking switches are closed slightly later to account for signal travel delays in the system. The RX blocking switches prevent the energizing signal that leaks into the receiver during the measurement cycle (specifically during the on time of the energizing signal) from entering the IF section. If the leakage signal enters the IF section, then it charges the IF section and the IF section may not settle out before the sensor signal arrives. For example, in one instance the IF section was charged for several hundred nanoseconds after the on time of the energizing signal. Blocking the leakage signal from the IF section eliminates this problem and improves detection of the sensor signal.

Base Unit Implementing Multiple Sampling Points

An alternative embodiment of the base unit uses multiple sampling points rather than the single sampling point discussed above in connection with FIG. 3. If a single sampling point is used and the sampling point coincides with a point where the average DC voltage of the phase detector is zero, then the system can lock even though the frequency is not the correct frequency. This situation can occur when there is system stress, such as a DC offset in the loop integrator or some other disturbance. The use of multiple sampling points helps prevent a false lock under these circumstances.

Figure 5:
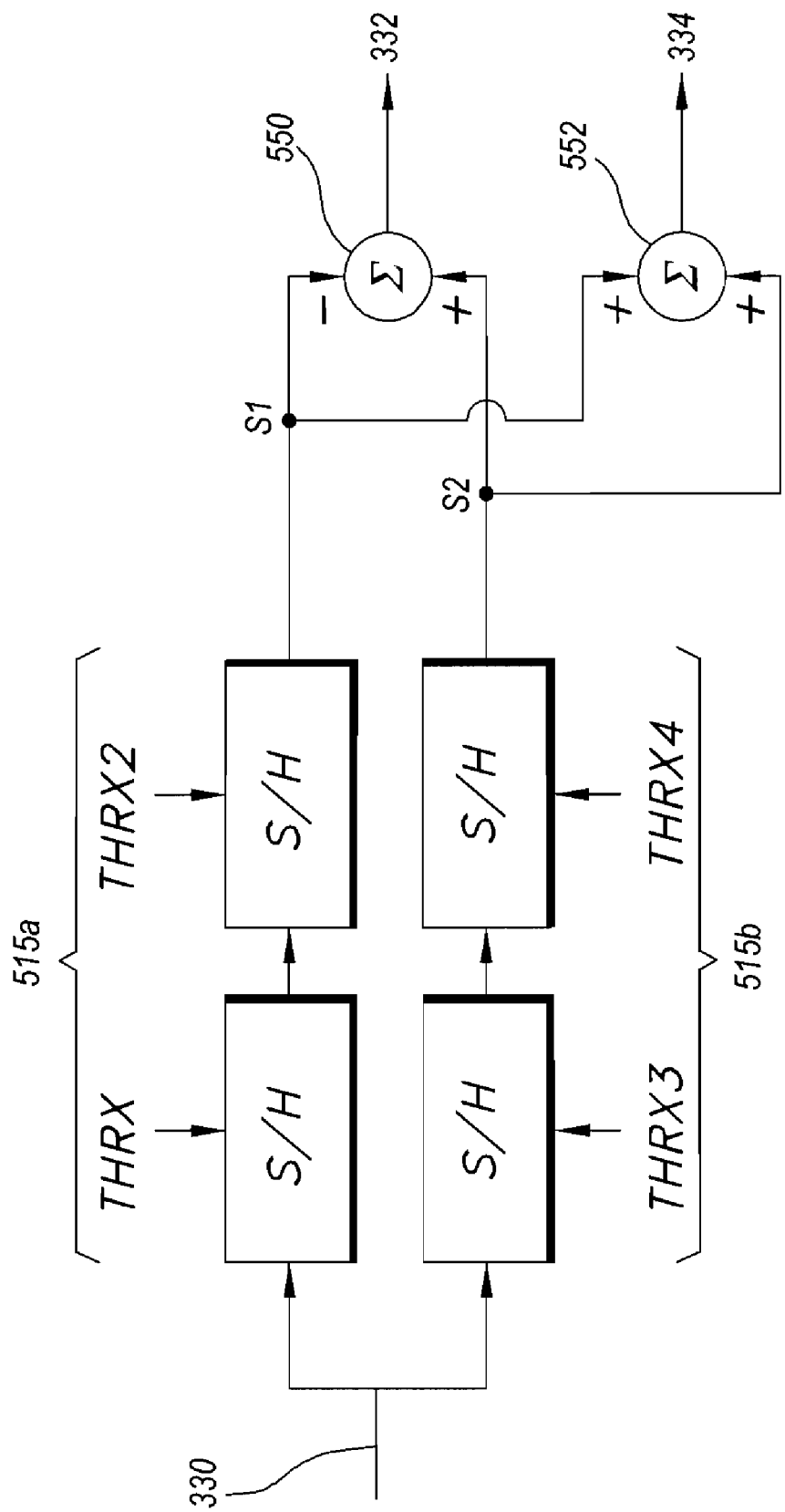
FIG. 5 is a block diagram of a portion of an exemplary base unit in accordance with an embodiment of the invention.

FIG. 5 illustrates a portion of the base unit for an embodiment that uses two sampling points, S1, S2. The components illustrated in FIG. 5 are used instead of the sample and hold components 314, 315 used in FIG. 3. As discussed above in connection with FIG. 3, this embodiment uses a pair of PLLs. The phase of the energizing signal is adjusted by the fast PLL and the frequency of the energizing signal is adjusted by the slow PLL. However, in this embodiment only a single cycle is needed to adjust the phase and frequency of the energizing signal, i.e. separate calibration and measurement cycles are not necessary. Since only a single cycle is used, the timing of the RX blocking switches is slightly different than that described above in connection with FIG. 3. In this embodiment, the RX blocking switches are generally closed during the off time of the energizing signal. The specific timing of the closure of the RX blocking switches may be system specific and can be adjusted to account for signal travel delays in the system.

The initial frequency and phase of the energizing signal are set as described above in connection with FIG. 3. The energizing signal may be blocked from the receiver during the on time of the energizing signal. During the off time of the energizing signal, the receiver is unblocked and the coupled signal from the sensor is received. The coupled signal is amplified and filtered through the receive section 311. The signal is down converted and additional amplification and filtering takes place in the IF section 312. In one embodiment, the signal is down converted to 4.725 MHz. After being processed through the IF section the signal is mixed with local oscillator 2 and sampled by the two sample and hold circuits 515a and 515b to determine the phase difference between the coupled signal and the energizing signal.

The two sample points are applied to a first differential amplifier 550 and a second differential amplifier 552. The first differential amplifier outputs a signal representing the difference between the two sampling points (S2−S1), which is fed into the loop filter 320 and used to adjust the frequency of the energizing signal. The second differential amplifier 552 outputs a signal representing the sum of the two sampling points (S1+S2), which is fed into the loop filter 316 and used to adjust the phase of the energizing signal The FPGA controls the timing of the two sample and hold circuits. In one embodiment, the first sample point occurs approximately 30 ns after the energizing signal is turned off and the second sample point occurs approximately 100 to 150 ns after the energizing signal is turned off. The timing of the first sampling point is selected so that the first sampling point occurs soon after the switching and filter transients have settled out. The timing of the second sampling point is selected so that there is sufficient time between the first sampling point and the second sampling point to detect a slope, but before the signal becomes too noisy.

The frequency of the energizing signal is deemed to match the resonant frequency of the sensor when the slow PLL is locked. Once the resonant frequency is determined, the physical parameter, such as pressure, is calculated using the calibration parameters associated with the sensor, which results in a difference frequency that is proportional to the measured pressure.

Base Unit Implementing Continuous Signal Processing

Another alternative embodiment of the base unit uses continuous signal processing techniques instead of the sampled processing techniques discussed above in connection with FIGS. 3 and 5. This embodiment derives continuous wave signals from the pulsed calibration signal and the pulsed sensor signal and uses the continuous wave signals to adjust the phase and frequency of the energizing signal.

Figure 6:
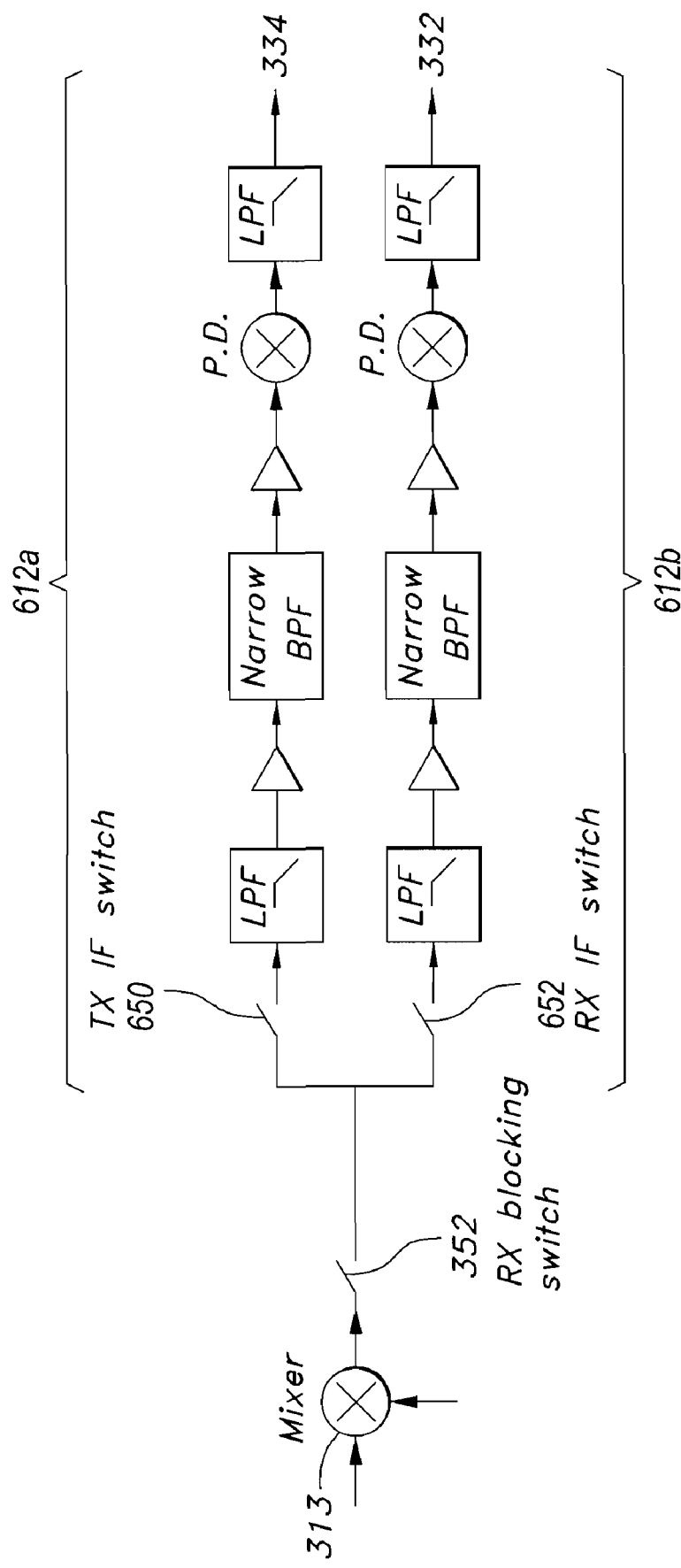
FIG. 6 is a block diagram of a portion of an exemplary base unit in accordance with another embodiment of the invention.

FIG. 6 illustrates a portion of the base unit for an embodiment that uses continuous signal processing. As illustrated by FIG. 6, this embodiment uses separate calibration 612a and measurement sections 612b instead of the common IF section 312 and separate sample and hold circuits 314 and 315 used in FIG. 3. After the signal passes through the receiver section 311, the mixer, and one of the RX blocking switches, the signal is split into a pair of switches, TX IF switch 650 and RX IF switch 652. The FPGA controls the switches (control signals not shown) so that the TX IF switch 650 is closed and the RX IF switch 652 is opened during the calibration cycle and the TX IF switch is opened and the RX IF switch is closed during the measurement cycle. The calibration section 612a and the measurement section 612b each include the aforementioned switch, a low pass filter, a narrow bandpass filter, amplifiers and a phase detector. The common IF section of FIG. 3 uses a bandpass filter, typically on the order of 2-3 MHz whereas the calibration and measurements sections of FIG. 6 use a narrow bandpass filter, typically on the order of 60-120 kHz.

The following description of the embodiment illustrated by FIG. 6 uses alternating calibration and measurement cycles. However, in other embodiments, the calibration cycle and the measurement cycle can be implemented in the same pulse repetition period.

During the calibration cycle, the calibration signal which enters the receiver 310 is processed through the receive section 311 and the calibration section 612a. The phase difference output from the calibration section is sent to the loop filter 316 and the adjustment of the phase of the energizing signal proceeds as described above in connection with FIG. 3.

During the measurement cycle, the energizing signal may be blocked from the receiver during the on time of the energizing signal. During the off time of the energizing signal, the receiver is unblocked and the sensor signal is received. The coupled signal is amplified and filtered through the receive section 311 and then transferred to the measurement section 612b. The phase difference output from the measurement section is sent to loop filter 320 and the adjustment of the frequency of the energizing signal proceeds as described above in connection with FIG. 3.

In one embodiment, the RX blocking switches close as described above in connection with FIG. 3, but open earlier during the measurement cycle. Instead of being closed through the end of the off time of the energizing signal, the RX blocking switches open before the end of the off time. The timing of the opening of the RX blocking switches is based on the sensor characteristics and is selected so that the switches open once the sensor signal falls below the noise level. Since most of the energy from sensor signal is received within a time period of $Q/f_o$, where $Q$ is the Q of the sensor and $f_o$ is the center frequency of the sensor, the RX blocking switches can be opened after approximately $Q/f_o$. For example, if the Q of the sensor if 40 and the fo is 32 MHz, then the RX blocking switches are opened after approximately 1.25 microseconds during the measurement cycle. The Q of the sensor and an approximate fo of the sensor are typically known and can be used to control the timing of the RX blocking switches.

In the embodiments that use sample and hold techniques, only the sampled information is used and the noise after the sample point(s) is ignored. However, in this continuous signal embodiment, all of the noise is seen unless other adjustments are made. Opening the RX blocking switches once the sensor signal decays below the noise level helps reduce the noise seen by the rest of the system and improves detection of the sensor signal.

The frequency spectrum of the sensor signal includes a number of spectral components that correspond to the pulse repetition frequency, including a strong component corresponding to the center frequency of the energizing signal (fo). The information needed to determine the resonant frequency of the sensor can be obtained by examining the phase of the spectral component that corresponds to fo. The measurement section isolates the spectral component at fo and the resulting time domain signal is a continuous wave signal.

In some embodiments, the system generates an energizing signal with a random or pseudo random frame width. For example, the pulse width is 2 microseconds for each frame, but the frame size is pseudo randomly selected from one of four possible frame sizes: 6.22 microseconds, 8.76 microseconds, 11.30 microseconds and 13.84 microseconds. The use of four frame sizes is exemplary. Any number of frame sizes can be used, although at some point increasing the number of possible frame sizes increases the system complexity with only incremental improvements.

The minimum frame sizes corresponds to the smallest frame size that provides a sufficient receive window and typically corresponds to the pulse width. For example, if the pulse width is 2 microseconds, then the minimum receive window is also 2 microseconds making the minimum frame size 4 microseconds. However, switching times and other practical considerations related to the components used may result in a slightly larger frame size. The maximum frame size is typically based on a desired average pulse repetition rate. In this example, if the average pulse repetition rate is selected as 10 microseconds, then the maximum frame size is 14 microseconds.

If a random or pseudo random frame width is used, then the frame width can vary between the calibration cycle and the measurement cycle or a common frame width can be used for a calibration cycle and the following measurement cycle. The use of a random or pseudo random frame width helps isolate the spectral component needed to determine the resonant frequency of the sensor and relaxes the requirements of the narrow bandpass filter used in the receive section.

As an alternative to the embodiment illustrated by FIG. 6, the RX blocking switch 352 is combined with the TX IF switch 650 and the RX IF switch 652 and the control of the TX IF and the RX IF switches are modified to accommodate the combination.

Identifying False Locks

The system provides unique solutions to the false lock problem. A false lock occurs if the system locks on a frequency that does not correspond to the resonant frequency of the sensor. There are several types of false locks. The first type of false lock arises due to the pulsed nature of the system and the second type of false lock arises due to room reflection or resonance.

Pulsatile False Lock

In one embodiment, the first type of false locks occur at approximately 500 kHz above and below the resonant frequency of the sensor. The frequency of the energizing signal is between 30-37.5 MHz with a pulse repetition frequency of 100 kHz and a duty cycle of 20%. Due to the characteristics of the system and the sensor, the system samples the sensor signal approximately 2.2 microseconds after the start of the energizing pulse to determine the phase difference between the sensor signal and the energizing signal. In one embodiment where the resonant frequency of the sensor is 36.36 MHz, a false lock can occur at 36.36 MHz±454 kHz, 36.36 MHz±908 kHz, 36.36 MHz±1362 kHz, etc.

If the frequency of the energizing signal matches the resonant frequency of the sensor at 36.36 MHz, then the frequency of the sensor signal is also 36.36 MHz. The sensor signal goes through approximately 80 cycles between the time when the phase of the energizing signal is 0 and the sampling point, which is approximately 2.2 microseconds later. In this situation, the phase of the sensor signal is 0 when it is sampled so the system locks.

However, if the resonant frequency of the sensor is 36.36 MHz and the frequency of the energizing signal is a multiple of 454 kHz above or below 36.36 MHz, then a false lock could occur if only the phase of the sensor signal at the sampling point is considered. For example, if the frequency of the energizing signal is 36.36 MHz+454 kHz, then the frequency of the sensor signal is not constant but is changing toward the resonant frequency of the sensor. The sensor signal goes through approximately 81 cycles between the time when the phase of the energizing signal is 0 and the sampling point. Even though the phase of the sensor signal is 0 when sampled, the system should not lock because the frequency does not represent the resonant frequency of the sensor.

Figure 7A:
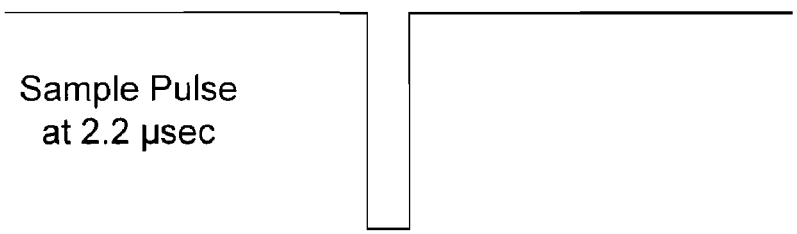
FIGS. 7(a), 7(b) and 7(c), collectively referred to herein as FIG. 7, illustrate sampling a signal without a beat frequency and a signal with a beat frequency using a single sampling point in accordance with an embodiment of the invention.
Figure 7B:
Figure 7C:

FIG. 7 illustrates the difference between a true lock condition and a false lock condition when the frequency of the energizing signal is approximately a multiple of 500 kHz above or below the resonant frequency of the sensor. FIG. 7(a) illustrates the sample pulse at approximately 2.2 microseconds after the start of the energizing pulse. FIG. 7(b) illustrates the sensor signal when the frequency of the energizing signal matches the resonant frequency of the sensor and shows that the phase of the sensor signal is 0 at the sampling point. FIG. 7(c) illustrates the sensor signal when the frequency of the energizing signal is off by approximately 500 kHz. FIG. 7(c) shows that the phase of the sensor signal is 0 at the sampling point, but that there is an unwanted beat frequency since the frequency of the energizing signal does not match the resonant frequency of the sensor.

Figure 8:
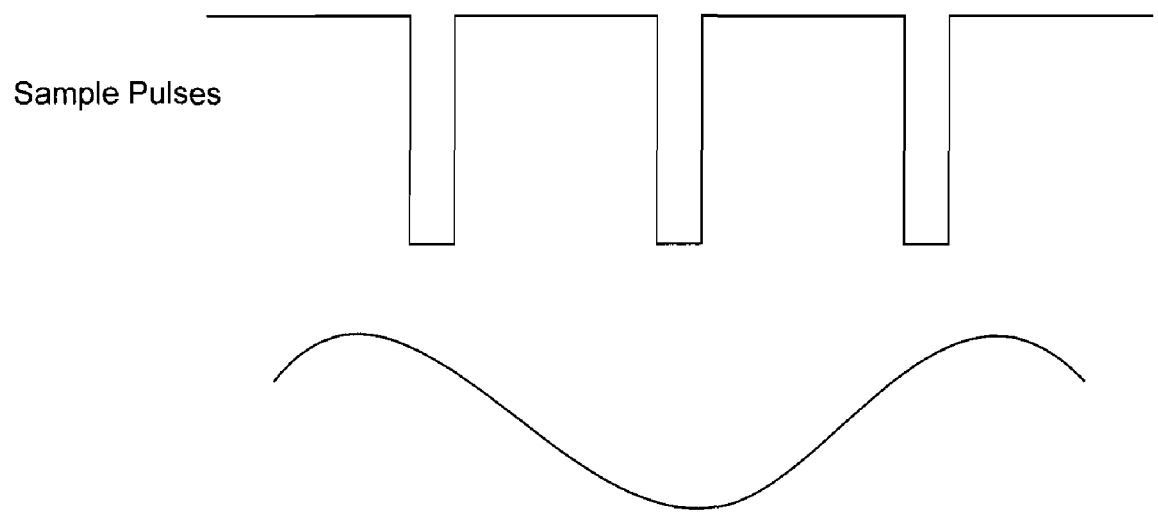
FIG. 8 illustrates sampling a signal with a beat frequency using multiple sampling points in accordance with an embodiment of the invention.

The present invention samples the phase of the sensor signal at multiple points to detect the beat frequency illustrated in FIG. 7(c). In the embodiment illustrated by FIG. 8, three sampling points are used. However, a different number of sampling points can be used so long as the sampling points are positioned to detect the beat frequency within the sensor signal. The spacing of the sampling points depends upon the frequencies where a false lock is anticipated. In one embodiment, three sample pulses are spaced approximately 800 nsec apart, i.e. 2.2 microseconds plus or minus 800 nsec. As shown in FIG. 8 the sample pulses sample the sensor signal at points where the phase is non-zero, if a beat frequency is present. The sampled values are averaged to determine whether there is a beat frequency. If the average of the sampled values is zero or greater, then the determination is that there is a beat frequency. If the average of the sampled values is less than zero, then the determination is that there is no beat frequency.

Referring back to FIG. 3, the sensor signal (after processing in the receive section 311 and the IF section 312) is mixed with local oscillator 2 and sampled to determine the phase difference between the sensor signal and the energizing signal. The sensor signal is also mixed with a 90 degree phase shift of local oscillator 2 at mixer 360. If the energizing signal matches the resonant frequency of the sensor, then the frequency of the sensor signal is constant and the output of mixer 360 is a constant dc voltage for the duration of the sensor signal, as shown in FIG. 7(b). However, if the energizing signal does not match the resonant frequency of the sensor, (e.g. the resonant frequency of the sensor is 36.36 MHz and the frequency of the energizing signal is 36.36 MHz+464 kHz), then the frequency of the sensor signal is changing and the output of the mixer 360 has a beat frequency, as shown in FIG. 7(c). The output of mixer 360 is sampled with multiple sampling points to detect the beat frequency.

Figure 9A:
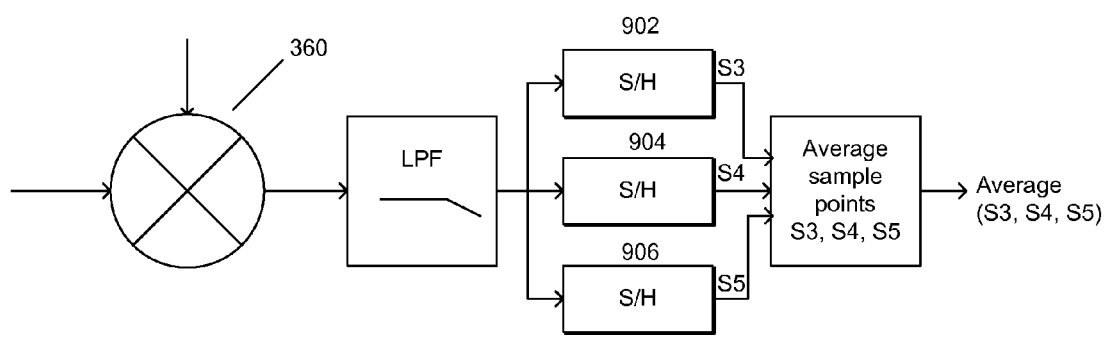
FIG. 9(a) is a block diagram of a portion of an exemplary base unit in accordance with an embodiment of the invention.

FIG. 9(a) illustrates a portion of an exemplary base unit that uses multiple sampling points to detect a beat frequency. The components illustrated in FIG. 9(a) can be used in addition to the signal strength components illustrated in FIG. 3 (LPF, S/H labeled THSS and S/H labeled THSS2) or can be used in place of the signal strength components. The output from mixer 360 is down converted and sampled multiple times within the same measurement cycle. The embodiment illustrated by FIG. 9(a) uses three sample and hold components 902, 904, 906 to obtain three points, S3, S4, S5 at three different times, t1, t2, t3, but a different number of sampling points can be used in other embodiments. The three sampling points are averaged and the average is used to detect a beat frequency.

Figure 9B:
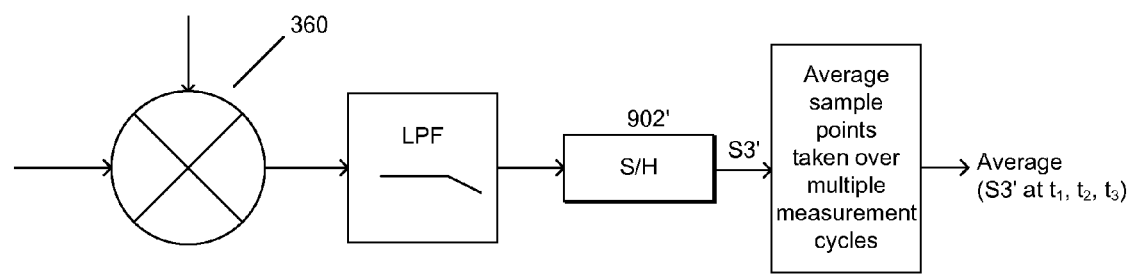
FIG. 9(b) is a block diagram of a portion of an exemplary base unit in accordance with another embodiment of the invention.

FIG. 9(b) illustrates an alternative to FIG. 9(a). In this embodiment, the sampling points are taken over multiple measurement cycles. Since the sensor signal does not change dramatically between consecutive measurement cycles, the sample points can be taken over multiple measurement cycles. The components illustrated in FIG. 9(b) can be used in addition to the signal strength components illustrated in FIG. 3 (LPF, S/H labeled THSS and S/H labeled THSS2) or can be used in place of the signal strength components. The output from mixer 360 is down converted and sampled once per measurement cycle until the desired number of sample points are obtained. For example, if three sample points are used, then the signal is sampled at three different points over three measurement cycles, i.e. the signal is sampled at t1 in the first measurement cycle, at t2 in the second measurement cycle and at t3 in the third measurement cycle. As in the embodiment illustrated by FIG. 9(a), the sampling points are averaged and the average is used to detect a beat frequency.

If a beat frequency is detected, then the frequency of the energizing signal should not be used to determine the resonant frequency of the sensor. In one embodiment, the system is not allowed to lock, in a second embodiment the system is allowed to lock, but an indication is provided to the physician using the system that there is a possibility of a false lock, and in a third embodiment, the system is allowed to lock, but the output of the system that represents either the frequency of the sensor or the physical parameter of interest is blocked. An example of the second embodiment is an indicator on the display that displays a particular color or a particular image when a beat frequency is detected. In response to seeing the particular color or particular image, the physician modifies the frequency of the energizing signal.

As described in more detail above in connection with FIG. 5, multiple sampling points can be used to sample the phase of the sensor signal. If there is a beat frequency at the output of mixer 360, there is also a beat frequency at point 330 and S1 is not equal to S2. If a beat frequency is not present, then S1 equals S2. A comparison of S1 and S2 can also help prevent false locks. Note that S1 plus S2 represents the average phase and can be used to calibrate the system if sampled while the system is transmitting to the sensor.

The use of multiple sampling points to detect a beat frequency in the sensor signal has been illustrated using particular frequencies and timings. As those skilled in the art will recognize, the invention contemplates other frequencies and timings. The frequencies and timings for other embodiments will depend upon the characteristics of the sensor and the system used to interrogate the sensor, including the pulse width of the energizing signal, the characteristics of the sensor and the sampling point(s) of the sensor signal.

Non-Pulsatile False Locks

The second type of false lock arises due to a reflection or resonance of another object in the vicinity of the system. Since the wireless sensor is implanted in the body, the sensor signal is typically pulsatile in nature due to the patient's blood pressure. The sensor signal is always pulsatile if the sensor measures properties associated with the heart and is usually pulsatile if the sensor measures properties associated with an abdominal aneurysm. Since the sensor signal is usually pulsatile, it is possible to detect a false lock due to reflection or resonance of another object by determining whether the coupled signal is pulsatile since most false locks due to room reflection or resonance are not pulsatile. The present invention compares the energy in different frequency bands of a signal representing the change of frequency of the energizing signal to determine if the coupled signal is pulsatile.

In one embodiment the system performs a time to frequency domain transform on a signal representing the change of frequency of the energizing signal. The transform can be performed using a FT (Fourier transform), cosine transform, sine transform, Hammond transform, wavelet transform, Laplace transform, bandpass filters (digital or analog), or using any other suitable method or components. Samples within certain predefined frequency ranges are analyzed to determine whether the energy in the frequency ranges meet certain predefined relationships. For example, whether the energy in the lower frequency range is greater than the energy in the higher frequency range. If the predefined relationship is met and continues for one or more sample periods, then the signal is deemed pulsatile.

Figure 10:
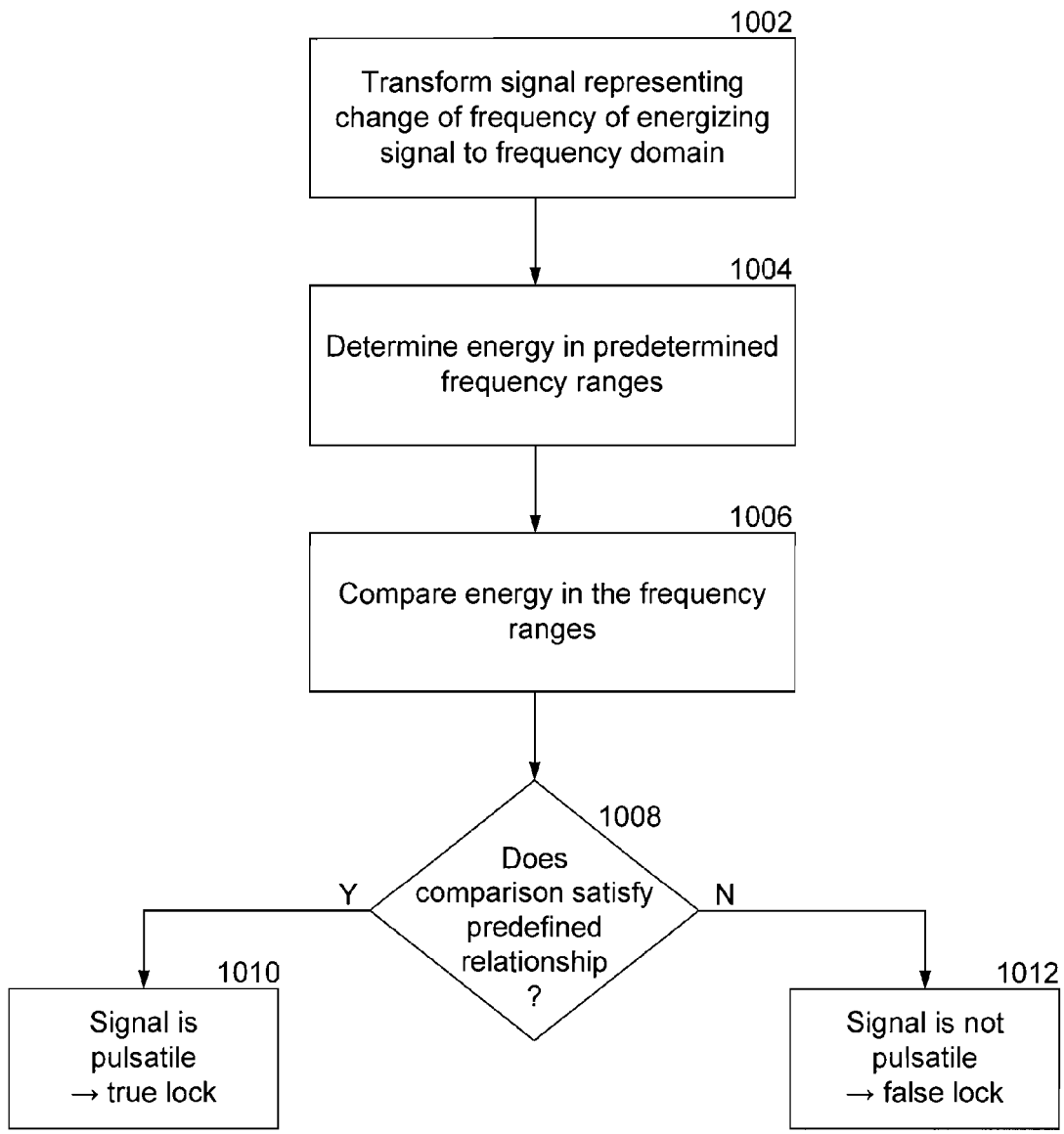
FIG. 10 is a flow diagram of a method for determining whether a signal is pulsatile in accordance with an embodiment of the invention.

FIG. 10 further illustrates the method for determining whether the signal is pulsatile. The signal representing the change of frequency of the energizing signal is transformed into the frequency domain using a FFT or other suitable method at 1002. The energy in certain predetermined frequency ranges is determined at 1004. In one embodiment, the maximum value within a lower frequency range and the maximum value within a higher frequency range are determined. However, different energy measurements can be used including composite energy, average energy or spectral density within a sub-range of the frequency range. The term energy used herein also includes power. The energy in the frequency ranges is compared at 1006. For example, the maximum values within the frequency ranges are compared. If the comparison satisfies a predefined relationship at 1008, then the signal is pulsatile and an indication of a true lock is provided at 1010. If the comparison does not satisfy the predefined relationship at 1008, then the signal is not pulsatile and an indication of a false lock is provided at 1012.

The following example illustrates the method of FIG. 10 for an embodiment where the pulsatile nature of the signal is based on blood pressure. In this example, a FT is performed at DDS1 on a signal representing the change of frequency of the energizing signal using 400 samples sampled at 240 Hz. Two sets of sample points representing two frequency ranges are selected from the sample points in a frequency range of 0 to 120 Hz. The two sets of sample points each include 20 sample points. The first set of 20 sample points corresponds to sample points 2-22 (corresponds approximately to 0.5-13 Hz) and the second set of 20 sample points corresponds to sample points 23-42 (corresponds approximately to 14-26 Hz). The first sample point is ignored since it corresponds to approximately DC. In an alternate embodiment, the first set of sample points corresponds to 0.5-2 Hz and the second set of sample points corresponds to 2-4.5 Hz. Since the period of a blood pressure waveform is between one and two seconds, the energy in the first frequency range is higher than the energy in the second frequency range when the signal includes characteristics corresponding to a blood pressure waveform. If the maximum of the first set of 20 sample points is at least twice the maximum of the second set of 20 sample points and this relationship continues for at least 2 seconds, then the signal is pulsatile.

Referring back to FIG. 3, the output of DDS1 represents the frequency of the energizing signal. This output of DDS1 can be used for the FT. The system sends a signal to the sensor approximately 50,000 times a second. However, it has been determined that analyzing the output frequency of DDS1 at approximately 240 points per second provides sufficient data to provide an accurate indication of systolic pressure and diastolic pressure and to identify characteristics, such as the diachrotic notch, in the blood pressure waveform. The analysis of the sample points can also be performed by directly sampling the output of DDS1. Alternatively, the analysis of the sample points can be performed by a comparison module, such as a comparator, divider or log amp.

If the signal is not pulsatile, then the frequency of the energizing signal should not be used to determine the resonant frequency of the sensor. In one embodiment, the system is not allowed to lock, in a second embodiment the system is allowed to lock, but an indication is provided to the physician using the system that there is a possibility of a false lock, and in a third embodiment, the system is allowed to lock, but the output of the system that represents either the frequency of the sensor or the physical parameter of interest is blocked. An example of the second embodiment is an indicator on the display that displays a particular color or a particular image when the signal is not pulsatile. In response to seeing the particular color or particular image, the physician modifies the frequency of the energizing signal.

The detection of a false lock using the pulsatile nature of a signal has been illustrated using blood pressure. However, any periodic physiological characteristic could be used and the invention is equally applicable to other fluidic pressures within the body, as well as other periodic characteristics.

The detection of a false lock has also been described using particular frequencies, timings, number and ranges of sample points and relationships. As those skilled in the art will recognize, the invention contemplates other frequencies, timings, number and ranges of sample points and relationships that will depend upon the particular application. For example, if the sensor is attached to a pump or to an engine, then the frequency characteristics associated with the proper operation of the pump or engine can be used to determine the appropriate frequencies, timings, number and ranges of sample points, and relationships. Although the frequency ranges used in the preceding example are adjacent, the invention contemplates the use of non-adjacent frequency ranges as well.

Additional alternative embodiments will be apparent to those skilled in the art to which the present invention pertains without departing from its spirit and scope. For example, the system can operate with different types of sensors, such as non-linear sensors that transmit information at frequencies other than the transmit frequency or sensors that use backscatter modulations. Accordingly, the scope of the present invention is described by the appended claims and is supported by the foregoing description.

What is claimed is:

1. A method for identifying a false lock, comprising:
generating an energizing signal with a first phase and a first frequency;
receiving a calibration signal;
determining a first phase difference between the calibration signal and the energizing signal;
based on the first phase difference adjusting the first phase of the energizing signal to reduce the first phase difference;
energizing a wireless sensor with an energizing signal having the first frequency;
receiving a sensor signal;
determining whether the sensor signal includes a predetermined beat frequency; and
if the sensor signal includes the predetermined beat frequency, then determining that the first frequency of the energizing signal corresponds to a false lock.

2. The method of claim 1, wherein determining whether the sensor signal includes a predetermined beat frequency comprises:
sampling the sensor signal using multiple sampling points;
determining an average of the multiple sampling points; and
based on the average, determining whether the sensor signal includes the predetermined beat frequency.

3. The method of claim 2, wherein determining whether the sensor signal includes the predetermined beat frequency, comprises:
if the average is zero or greater, then determining that the sensor signal includes the predetermined beat frequency;

otherwise, determining that the sensor signal does not include the predetermined beat frequency.

4. The method of claim 2, wherein the multiple sampling points comprise three sampling points and wherein a second sampling point is approximately 2.2 microseconds after the start of the energizing signal that energizes the sensor, a first sampling point is approximately 800 ns prior to the second sampling point and a third sampling point is approximately 800 ns after the second sampling point.

5. The method of claim 2, wherein the multiple sampling points occur within a single measurement cycle.

6. The method of claim 2, wherein the multiple sampling points occur in consecutive measurement cycles.

7. The method of claim 1, wherein the predetermined beat Frequency corresponds to a multiple of approximately 500 kHz above or below a resonant frequency of the sensor.

8. The method of claim 1, wherein the beat frequency is based on a pulse width of the energizing signal and characteristics of the sensor.

9. The method of claim 1, further comprising:
if the sensor signal includes the predetermined beat frequency, then providing an output to a user indicating a false lock.

10. A method for identifying a false lock, comprising:
energizing a wireless sensor with an energizing signal having a first frequency;
receiving a sensor signal;
sampling the sensor signal using multiple sampling points;
determining whether the sensor signal includes a predetermined beat frequency; and
if the sensor signal includes the predetermined beat frequency, then determining that the first frequency of the energizing signal corresponds to a false lock.

11. The method of claim 10, wherein the predetermined beat frequency corresponds to a multiple of approximately 500 kHz above or below a resonant frequency of the sensor.

12. The method of claim 10, wherein determining whether the sensor signal includes a predetermined beat frequency comprises:
determining an average of the multiple sampling points;
if the average is zero or greater, then determining that the sensor signal includes the predetermined beat frequency; and
if the average is less than zero, then determining that the sensor signal does not include the predetermined beat frequency.

13. The method of claim 10, further comprising:
if the sensor signal includes the predetermined beat frequency, then providing an output to a user indicating a false lock.

14. The method of claim 10, wherein the multiple sampling points occur within a single cycle.

15. The method of claim 10, wherein the multiple sampling points occur in consecutive cycles.

* * * * *